United States Patent [19]

Schlaeppi et al.

[11] Patent Number: 5,272,059

[45] Date of Patent: Dec. 21, 1993

[54] MONOCLONAL ANTIBODIES SPECIFIC FOR HIRUDIN

[75] Inventors: Jean-Marc Schlaeppi; Dietmar G. Braun, both of Basel, Switzerland

[73] Assignee: Ciba-Geigy Corporation, Ardsley, N.Y.

[21] Appl. No.: 920,025

[22] Filed: Jul. 27, 1992

Related U.S. Application Data

[63] Continuation of Ser. No. 467,103, Jan. 18, 1990, abandoned.

[30] Foreign Application Priority Data

Jan. 25, 1989 [GB] United Kingdom ............... 8901600
May 10, 1989 [GB] United Kingdom ............... 8910713

[51] Int. Cl.$^5$ .................... C12Q 1/00; G01N 33/53; C07K 15/28
[52] U.S. Cl. ................... 435/7.9; 435/70.21; 435/240.27; 436/512; 436/518; 436/538; 530/388.25; 530/391.3
[58] Field of Search ............ 530/387, 388.25; 435/971, 240.26, 7, 9; 436/538, 518

[56] References Cited

PUBLICATIONS

Hudson et al. *Practical Immunology* Blackwell Scientific Pub., Oxford, Great Britain 1976, pp. 2–5.
S. Spinner et al. J. Immunol., Methods 87, 79 (1986).
G. Stöffler et al., Thrombosis Research, Suppl. VII, 38 (1987).
S. Spinner et al. Biol. Chem. Hoppe-Seyler 367, Suppl. 254 (1986).
F. Scheffauer et al., Biol. Chem Hoppe-Seyler 367, Suppl., 255 (1986).
S. Spinner et al. Biol. Chem. Hoppe-Seyler 369, 921 (1988).
S. Spinner et al., Eur. J. Clin. Invest 18, A7 (1988).
S. Spinner et al., Thrombosis Research 51, 617 (1988).
S. J. T. Mao et al., J. Immunol. Methods 120, 45 (1989).

*Primary Examiner*—Sam Rosen
*Attorney, Agent, or Firm*—W. Murray Spruill; JoAnn Villamizar

[57] ABSTRACT

The invention concerns a process for the preparation of hybridoma cells which secrete monoclonal antibodies specific for hirudin, the hybridoma cells themselves, the monoclonal antibodies specific for hirudin secreted by these hybridoma cells, derivatives thereof, and a process for the preparation of said antibodies and derivatives. These monoclonal anti-hirudin antibodies and their derivatives are useful for the determination of hirudin and as an antidote to hirudin. The invention also concerns test kits and pharmaceutical compositions comprising said monoclonal antibodies and/or derivatives.

13 Claims, 2 Drawing Sheets

MONOCLONAL ANTIBODIES SPECIFIC FOR HIRUDIN

This application is a continuation of application Ser. No. 467,103, filed Jan. 18, 1990, now abandoned.

The invention concerns a process for the preparation of hybridoma cells which secrete monoclonal antibodies specific for hirudin, the hybridoma cells themselves, the monoclonal antibodies specific for hirudin secreted by these hybridoma cells and derivatives thereof, and a process for the preparation of said antibodies and derivatives. Furthermore, the invention relates to the use of the monoclonal antibodies specific for hirudin and/or derivatives thereof for the determination of hirudin and as an antidote to hirudin, to test kits and pharmaceutical compositions comprising the antibodies and/or derivatives.

BACKGROUND OF THE INVENTION

An efficiently operating haemostatic system is of vital necessity for the mammalian organism. In healthy organisms, defects of the blood vascular system, e.g. vascular lesions, are repaired in a two-step process: the aggregation of thrombocytes is followed by the formation of a fibrin clot in an enzyme cascade under participation of several blood clotting factors. Most of these factors are serin proteases, for example thrombin which catalyzes the reaction of fibrinogen to fibrin. The coagulation system is counteracted by the fibrinolytic system involving, among others, the protease plasmin which cleaves fibrin. The fibrinolytic system is equally important as the coagulation system since even under normal physiological conditions small amounts of fibrin are formed in the blood and therefore intravascular thrombi would be formed without constant fibrinolysis. Furthermore, the fibrinolytic system is necessary in keeping tubular systems, such as glandular ducts and the efferent urinary tract, free from fibrin precipitates and in dissolving fibrin clots after the structural integrity of a damaged area is restored. The coagulation and fibrinolytic systems are usually in a dynamic equilibrium. In cases, however, in which the fibrinolytic potential of the organism is disturbed or insufficient, for example in patients suffering from thromboembolisms or post-operative complications, it is indispensable to support the organism by the administration of anticoagulants to prevent further formation of fibrin and of thrombolytic agents to dissolve the formed thrombi.

Hirudin, an anticoagulant that occurs naturally in leeches (*Hirudo medicinalis*), has been known for a long time. Hirudin is not a single polypeptide species but a class of equally acting polypeptides consisting of at least four representatives designated hirudin variant 1 (HV1), hirudin variant 2 (HV2; EP Application 0 158 564), hirudin variant PA (HV3; PCT Application WO 88/03493), and "des-(Val)$_2$-hirudin" (EP Application 0 158 986). The variants differ from each other by a number of amino acids, for example at the N-terminal sequence which is Val-Val-Tyr for HV1, Ile-Thr-Tyr for HV2 and PA and Thr-Tyr for "des-(Val)$_2$-hirudin". Based on NMR studies, HV1 is composed of an N-terminal core domain with a protruding "finger" (residues 31-36), and an acidic terminal loop (Clore et al., EMBO Journal 6, 529, 1987). All above-mentioned hirudin variants have an accumulation of hydrophobic amino acids at the N-terminus and an accumulation of polar amino acids at the C-terminus, a tyrosine residue (Tyr 63) present as sulphate monoester, three disulphide bridges and the anticoagulant activity in common.

Of all naturally occurring and synthetic anticoagulants which are specific for thrombin, hirudin has the highest affinity for the target enzyme. The inhibitor forms an extremely stable one-to-one molar complex with thrombin which is enzymatically totally inactive. Other enzymes of the coagualation cascade are not inhibited by hirudin.

Hirudin shows promising pharmacokinetic and pharmacodynamic properties (see for example Markwardt et al., Thromb. Haemostasis 47, 226, 1982). No effects on heart rate, respiration, blood pressure, thrombocyte count, fibrinogen and haemoglobin were observed after intravenous administration of hirudin to dogs, even in high doses. In tests on rats, pigs and dogs, hirudin has proved effective in experimental thrombosis, in endotoxin shock, and also in disseminated intravascular coagulation.

One prerequisite for the therapeutic application of hirudin is the possibility to produce sufficient amounts using modern methods of biotechnology. Recently, cDNAs and synthetic genes coding for hirudin variants have been cloned and expressed in microbial hosts. Although the expression products lack the sulphate monoester group at Tyr 63 and were therefore designated desulphatohirudins, they turned out to exhibit biological properties at least equivalent to those of natural sulphated hirudins. Desulphatohirudin variant HV1 bas been expressed in *Escherichia coli* (EP Applications 0 158 564 and 0 168 342) and in *Saccharomyces cerevisiae* (EP Applications 0 168 342, 0 200 655, 0 225 633 and 0 252 854). Similarly, desulphatohirudin HV2 has been expressed in *E. coli* (EP Application 0 200 655, PCT Application WO 86/01224), and des-(Val)$_2$-desulphatohirudin has been expressed in E. coli (EP Application 0 158 986).

Equally important for future routine administration of the clotting inhibitor is the development of methods for sensitive and reproducible quantitation of the anticoagulant in biological fluids to be able to monitor the drug. Usually, hirudin is assessed via its interaction with thrombin. Due to the fact that hirudin is a very poor immunogen, it has hitherto been problematic to produce antibodies against hirudin which could be used in immunoassays for the determination of the anticoagulant. The European Patent Application 0 168 342 claims monoclonal antibodies specific for hirudin. However, the specification of the application does not contain a characterization of the claimed antibodies which are supposedly elicited against unmodified hirudin. In view of the poor immunogenic properties of hirudin, the conceptual approach to the production of anti-hirudin monoclonal antibodies in the above-cited patent application lacks the basis for a successful immunization procedure and thus, the successful production of such antibodies. Spinner et al. (J. Immunol. Methods 87, 79, 1986) describe the production of polyclonal anti-hirudin antibodies (antisera) by immunization of sheep with hirudin. The article expressly notes the limited success of the immunization procedure and the difficulties in producing antisera at all. The same research group describes three monoclonal antibodies to hirudin (Stöffler et al., Thrombosis Res. *Suppl.* 7, 38, 1987), one of which interferes with the interaction of hirudin with α-thrombin. However, neither the immunization procedure, especially the hirudin variant used as antigen, nor the interaction between the monoclonal antibody and the hirudin/α-thrombin complex are further characterized in the communication.

OBJECT OF THE INVENTION

It is the object of the present invention to produce monoclonal antibodies specific for natural and recombinant hirudin. This object is achieved by coupling hirudin to a suitable carrier to improve its immunogenicity, using said immunogenic hirudin-conjugate to immunize a suitable mammal, and fusing antibody-secreting cells of said mammal with cells of a continuous cell line, thus producing hybridoma cells which secrete the described monoclonal antibodies specific for natural and recombinant hirudin. The immunization procedure using immunogenic hirudin-conjugates results in high yields of the desired antibodies. Depending on the nature of the hirudin variant used in the immunization procedure, it is possible to produce a panel of monoclonal antibodies with specificities and high affinities to different hirudin variants. They are useful for the qualitative and quantitative determination of natural and recombinant hirudin, for example in immunoassays, and most of them can be employed for the differentiation of birudin variants due to lack of cross-reactivity with hirudin variants other than the variant used for immunization. Surprisingly, it was found that some of the monoclonal antibodies of the invention are also highly efficient in neutralizing the anti-coagulation activity of hirudin and can therefore be used as an antidote to hirudin to survey and regulate the effect of the anti-coagulant.

DESCRIPTION OF THE INVENTION

The invention concerns a process for the preparation of hybridoma cells which secrete monoclonal antibodies specific for hirudin, preferentially for recombinant hirudin, characterized in that a suitable mammal is immunized with an immunogenic hirudin-conjugate, preferentially with an immunogenic recombinant birudin-conjugate, antibody producing cells of said mammal are fused with cells of a continuous cell line, the hybrid cells obtained in the fusion are cloned, and cell clones secreting the desired antibodies are selected.

Preferred is a process according to the invention for the preparation of hybridoma cells which secrete monoclonal antibodies specific for hirudin variant HV1, in particular recombinant hirudin variant HV1 (rHV1), characterized in that the mammal is immunized with an immunogenic hirudin variant HV1-conjugate, in particular an immunogenic recombinant hirudin variant HV1 (rHV1)-conjugate.

In this process, the immunization procedure, i.e. the method how antibodies are elicited, is of great importance, especially in view of the immense variation in immunization schedules known in the art. It is of special interest to note that immunogenicity is determined not only by the nature of the antigen, but also by the characteristics of the responding individual and the manner in which the antigen is presented.

In accordance with the process of this invention, the antigen used is an immunogenic hirudin-conjugate. In the present application, the term hirudin, when not otherwise stated, is intended to embrace
(1) all naturally occurring or synthetic hirudin variants and hirudin derivatives, such as hirudin fragments, and
(2) all recombinant hirudin (desulphatohirudin) variants and recombinant hirudin (desulphatohirudin) derivatives, such as C-terminally shortened desulphatohirudins,
which are described in the literature or are obtainable by methods of recombinant DNA technology.
Examples of such hirudins are:
(a) a hirudin variant of type HV1 with the formula

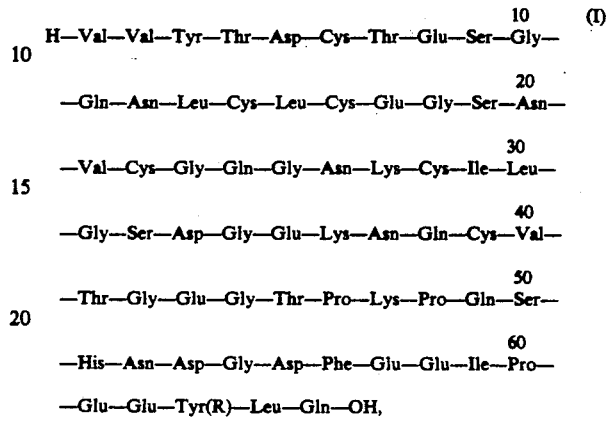

wherein
(R) is the phenolic hydroxygroup of Tyr (desulphatohirudin) or a —O—SO$_3$H, group, and/or
Lys 27 is replaced by Ile or Glu or
Lys 36 is replaced by Ile or Glu or
Lys 47 is replaced by Ile or Glu or
His 51 is replaced by Leu or Asp or
Val 1-Val 2 are replaced by Thr or
the whole molecule is shortened by Gln 65 or by Leu 64 and Gln 65;
(b) a hirudin variant of type HV2 with the formula

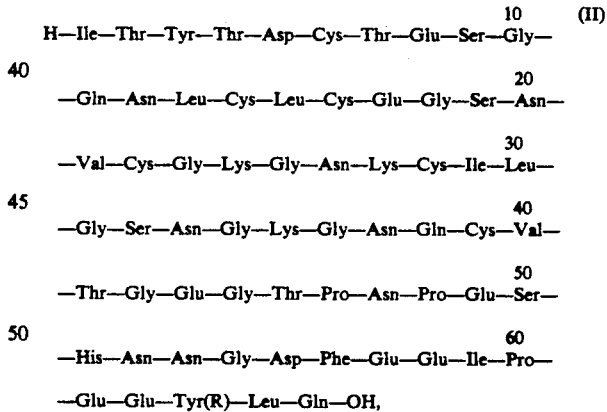

wherein
(r) is the phenolic hydroxygroup of Tyr (desulphatohirudin) or a —O—SO$_3$H group, and/or
Ile 1 is replaced by Val and Thr 2 by Val or
Asn 47 is replaced by Lys or Arg or His or
Tyr 63 is replaced by Glu or Asp;
(c) a hirudin variant of type PA (HV3) with the formula

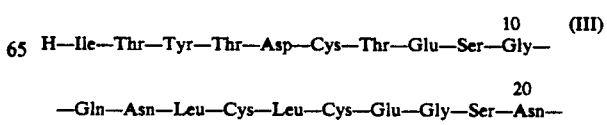

—Gln—Asn—Leu—Cys—Leu—Cys—Glu—Gly—Ser—Asn—

```
                                          30
—Val—Cys—Gly—Lys—Gly—Asn—Lys—Cys—Ile—Leu—

40
—Gly—Ser—Gln—Gly—Lys—Asp—Asn—Gln—Cys—Val—

50
—Thr—Gly—Glu—Gly—Thr—Pro—Lys—Pro—Gln—Ser—

60
—His—Asn—Gln—Gly—Asp—Phe—Glu—Pro—Ile—Pro—

—Glu—Asp—Ala—Tyr(R)—Asp—Glu—OH,
``` wherein (R) is the phenolic hydroxygroup of Tyr (desulphatohirudin) or a —O—SO₃H group, and/or
the polypeptide chain is shortened at the C-terminus by 18, 10, 9, 6, 4 or 2 amino acids, or
the polypeptide chain is shortened at the N-terminus by 1 or 2 amino acids.

If antibodies directed against a specific predetermined epitope of the hirudin molecule are desired, immunization with a conjugate of a hirudin fragment is possible. Such fragments are for example those consisting of amino acid residues 40-65 or 52-65 of rHV1. The fragments used for immunization need not have thrombin inhibiting activity.

The coupling of the antigen to a carrier to form an immunogenic hirudin-conjugate is necessary to enhance the immunogenicity of hirudin which is only a weak immunogen by itself. Suitable carrier molecules are for example lysine rich proteins with free amino groups available for coupling, especially high molecular weight proteins like bovine serum albumin (BSA; MW 66,200), alpha-amylase from *Bacillus subthis* (MW 58,000) or keyhole limpet haemocyanin (KLH; Mw>1,000,000) which are commercially available in large quantities. Porcine thyroglobulin, toxins such as tetanus-, cholera- or diphteria-toxins, human serum albumin (HSA), beta-2 microglobulin, and the like, may also be used as carriers. Purified rabbit IgG fraction against mouse IgG(H+L) (Kawamura & Berzofsky, J. Immunol. 136, 58, 1986) may also be employed as a carrier. Other possible carrier molecules include polysaccharides, natural or synthetic lipopolysaccharides, synthetic polypeptides such as polylysine, activated membranes, latex particles, bacteria such as Salmonella, and the like.

Preferred is an immunogenic hirudin-conjugate, in which hirudin, particularly recombinant hirudin, is coupled to bovine serum albumin (BSA) or to keyhole limpet haemocyanin (KLH), especially to BSA. Particularly preferred is an immunogenic hirudin-conjugate in which hirudin variant HV1, particularly recombinant hirudin variant HV1 (rHV1), is coupled to BSA or to KLH, especially to BSA.

The hirudin-conjugates of the invention are prepared by methods known per se, either by adsorption of hirudin to the carrier or by coupling using periodate, glutaraldehyde, carbodiimides e.g. N,N'-o-phenylenedimaleimide, N-(m-maleimidobenzoyloxy)-succinimide, N-(3-[2'-pyridyldithio]-propionoxy)-succinimide, N-ethyl-N'-(3-dimethylaminopropyl)-carbodiimide or the like. If coupling via carboxyl groups is intended, the amino groups of hirudin may first be protected, e.g. by acylation, for example with acetyl or tertiary butoxycarbonyl groups.

The immunogenic hirudin-conjugate may be mixed with adjuvants, i.e. agents that will further increase the immune response, for the immunization procedure. Possible adjuvants are Freund's complete adjuvant (emulsion of mineral oil, water, and mycobacterial extracts), Freund's incomplete adjuvant (emulsion of water and oil only), aluminium hydroxide gels etc.

The immunogenic hirudin-conjugate is used to immunize suitable mammals which recognize the conjugate as a foreign molecule, especially mice or rats, preferentially mice. Particularly preferred are Balb/c mice.

The routes of immunization include, among others, intradermal, subcutaneous, intramuscular, intraperitoneal, intravascular and intracranial injections. Since high antibody titers are desired, a series of injections is commonly given. The immunization is for example performed by injecting the immunogenic hirudin-conjugate, optionally mixed with incomplete or complete Freund's adjuvant, three to eight times parenterally, e.g. intraperitoneally and/or subcutaneously, in amounts of 10–20 μg into Balb/c mice at intervals of 1–3 weeks, followed by a booster injection of about 50–100 μg 1–3 months after the last immunization.

Antibody-producing cells of the immunized mammals, preferably lymphoid cells such as spleen lymphocytes, taken for example 3–5 days after the final booster injection, are fused with the cells of a continuous cell line, i.e. a continuously replicating cell clone which confers this replication ability to the hybrid cells resulting from the fusion. It is preferable to use a continuous cell line, e.g. a tumor cell line (myeloma), which meets the following requirements:

(1) The cell line does not itself produce immunoglobulins or fragments thereof but has the potential to produce and secrete large amounts of antibody.
(2) The cell line should lead to a high frequency of fused cell clones.
(3) The cell line carries a genetic marker so that the hybrid cells can be selected against non-fused parent cells, for example sensitivity to hypoxanthine, aminopterin and thymidine (HAT) medium (thymidine kinase [TK] or hypoxanthine (guanine) phosphoribosyl transferase [H(G)PRT] negative cells), ouabain resistance etc.

Preferred are murine myeloma cell lines which meet these requirements, particularly the mouse myeloma cell lines Sp2/0-Ag14 (Shulman et al., Nature 276, 269, 1978) or X63-Ag8.653 (Kearney et al., J. Immunol. 123, 1548, 1979) which are commercially available (Flow), or the mouse myeloma cell line PAI (Stocker et al., Hoffmann-LaRoche Research Disclosure No. 21713, 1982).

The fusion is performed in the presence of a fusion promoter, for example Sendai virus or other paramyxo viruses, optionally in UV-inactivated form, or chemical fusogens such as calcium ions, surface-active lipids, e.g. lysolecithin, and especially polyethylene glycol (PEG). Preferentially, the myeloma cells are fused with a three- to twentyfold excess of spleen cells from immunized mammals in a solution containing about 30–60 % polyethylene glycol of a molecular weight between 1000 and 4000.

After the fusion, the cells are resuspended and cultivated in a selective medium, for example in the case of TK or H(G)PRT negative parent myeloma cells in HAT medium. In this medium, only hybridoma cells will survive, because they combine the ability to grow and replicate in vitro like the parent myeloma cells and the HGPRT or TK genes essential for the survival in the HAT medium derived from the antibody-producing spleen cells of the immunized mammals.

4049-83-12, MAb 4114-96-1, MAb 4120-37-7 and MAb 4102-21-14, respectively.

TABLE 1

| hybridoma designation | antigen used for immunization | fusion partners | deposition number (ECACC) | deposition date |
|---|---|---|---|---|
| 4049-83-12 | BSA-rHV1 | B lymphocytes of Balb/c mice × Sp2/O—Ag14 | 8808 2504 | August 25, 1988 |
| 4114-96-1 | KLH-rHV1 peptide 40-65 | B lymphocytes of Balb/c mice × PAI | 8903 2102 | March 21, 1989 |
| 4120-37-7 | KLH-rHV1 peptide 40-65 | B lymphocytes of Balb/c mice × PAI | 8903 2103 | March 21, 1989 |
| 4102-21-14 | KLH-rHV1 peptide 52-65 | B lymphocytes of Balb/c mice × PAI | 8903 2101 | March 21, 1989 |

Abbreviations:
rHV1 — recombinant hirudin variant HV1
BSA — bovine serum albumin
KLH — keyhole limpet haemocyanin Suitable culture media for the cloning of hybridoma cells are the standard culture media, such as Dulbecco's modified Eagle medium (DMEM), minimum essential medium, RPMI 1640 medium and the like, optionally replenished by a mammalian serum, e.g. 10 to 15% foetal calf serum. Preferentially feeder cells, e.g. normal mouse peritoneal exudate cells, spleen cells, bone marrow macrophages, or the like, are added at the beginning of the cell growth immediately after the fusion step to nourish the hybridoma cells and support their growth, especially where cell densities are low, by providing growth factors and the like. If phagocytic cells such as macrophages or monocutes are used, they can perform a helpful service in cleaning up the debris of dead myeloma cells always found after aminopterin treatment. The culture media are supplemented with selective medium at regular intervals in order to prevent myeloma cells from overgrowing the hybridoma cells.

The hybridoma cell culture supernatants are screened for the desired monoclonal antibodies, preferentially by an enzyme immunoassay or radioimmunoassay. Positive hybridoma cell lines are cloned, e.g. by limiting dilution or in soft agar, preferentially twice or more. Optionally, hybridoma cells are passaged through animals, e.g. mice, by intraperitoneal injection and harvesting of ascites, which stabilizes hybridomas and improves growth characteristics. The cloned cell lines may be frozen in a conventional manner.

The invention further concerns hybridoma cells which are prepared by a process as hereinbefore described. The hybridoma cell lines of the invention are genetically stable, secrete monoclonal antibodies specific for hirudin of constant specificity and can be activated from deep-frozen cultures by thawing and recloning. Preferred are hybridoma cells secreting monoclonal antibodies specific for recombinant hirudin. Particularly preferred are hybridoma cells which secrete monoclonal antibodies specific for the hirudin variant HV1, especially recombinant hirudin variant HV1 (rHV1). Also preferred are the hybridoma cell lines with the designation 4049-83-12, 4114-96-1, 4120-37-7 and 4102-21-14, respectively. These cell lines have been deposited at the European Collection of Animal Cell Cultures (ECACC), PHLS Centre of Applied Microbiology & Research, Porton Down, Salisbury, Wilts. SP4 OJG, U.K., and are defined and identified by their deposition numbers in Table 1 below. They secrete the monoclonal antibodies with the designation Mab 4049-83-12, MAb 4114-96-1, MAb 4120-37-7 and MAb 4102-21-14, respectively.

Equally preferred are hybridoma cells which secrete monoclonal antibodies with a dissociation constant ($K_D$) for recombinant hirudin variant HV1 (rHV1) in the range of from $1.5 \times 10^{-9}$M (mol/liter) to $6 \times 10^{-10}$M. Also preferred are hybridoma cells which secrete monoclonal antibodies which recognize an epitope of recombinant hirudin variant HV1 (rHV1) comprising the amino acid residues 43 and 47 or the amino acid residues 61 and 62.

The invention also concerns novel monoclonal antibodies specific for hirudin, especially for recombinant hirudin, characterized in that they are secreted by hybridoma cells as described hereinbefore, and derivatives of such antibodies, preferably such monoclonal antibodies themselves. Preferred are monoclonal antibodies specific for the hirudin variant HV1, especially recombinant hirudin variant HV1 (rHV1). Particularly preferred are monoclonal antibodies of the invention which are of the IgG isotype, especially of the IgG1 or IgG2b isotype.

Most particularly preferred are monoclonal antibodies of the invention which neutralize the anticoagulation activity of hirudin towards α-thrombin, i.e. which exhibit antidote activity with respect to the effects of hirudin.

The neutralizing activity of the monoclonal antibodies of the invention can be determined using methods known in the art, for example with the coagulation assay by Fenton & Fasco (Thrombosis Res. 4, 809, 1974), or with a chromogenic substrate assay, e.g. the Chromozym TH assay (Boehringer).

Especially preferred are monoclonal antibodies with a dissociation constant (KD for recombinant hirudin variant HV1 (rHV1) in the range of from $1.5 \times 10^{-9}$M (mol/liter) to $6 \times 10^{-10}$M. Also preferred are monoclonal antibodies which recognize an epitope of recombinant hirudin variant HV1 (rHV1) located in the N-terminal core domain, in particular an epitope comprising the amino acid residues 43 and 47. Also preferred are monoclonal antibodies which recognize an epitope of recombinant hirudin variant HV1 (rHV1) close to the C-terminus, in particular an epitope comprising the amino acid residues 61 and 62.

Especially preferred are the monoclonal antibodies with the designation MAb 4049-83-12, MAb 4114-96-1, MAb 4120-37-7 and MAb 4102-21-14, respectively, which are secreted by the hybridoma cell lines with the designation 4049-83-12 (ECACC 8808 2504), 4114-96-1 (ECACC 8903 2102), 4120-37-7 (ECACC 8903 2103) and 4102-21-14 (ECACC 8903 2101), respectively, as described hereinbefore. MAb 4049-83-12 and MAb 4120-37-7 are capable of neutralizing the anticoagulation activity of hirudin. MAb 4049-83-12, which is a divalent antibody, totally neutralizes the anticoagulation activity of hirudin when MAb 4049-83-12 is present in half the amount of hirudin variant rHV1.

The invention further concerns derivatives of monoclonal antibodies of the invention, which retain their specificity for the antigenic determinants of hirudin. Preferred are derivatives of monoclonal antibodies of the invention with a dissociation constant ($K_D$) for recombinant hirudin variant HV1 (rHV1) in the range of from $1.5 \times 10^{-9}$M (mol/liter) to $6 \times 10^{-10}$M. Also preferred are derivatives of monoclonal antibodies of the invention which recognize an epitope of recombinant hirudin variant HV1 (rHV1) comprising the amino acid residues 43 and 47 or the amino acid residues 61 and 62. Especially preferred are derivatives of MAb 4049-83-12, MAb 4114-96-1, MAb 4120-37-7 and MAb 4102-21-14. Examples of such derivatives are conjugates of the monoclonal antibodies with an enzyme, a fluorescence marker, a metal chelate, a chemiluminescent marker, avidin, biotin or the like, or radioactively labelled monoclonal antibodies or antibody fragments.

Enzymes used for antibody conjugates of the invention are, for example, horseradish peroxidase, alkaline phosphatase, $\beta$-D-galactosidase, glucose oxidase, glucoamylase, carboanhydrase, acetylcholinesterase, lysozyme, malate dehydrogenase or glucose-6-phosphate dehydrogenase. Fluorescent markers conjugated with the monoclonal antibodies of the invention are fluorescein, fluorochrome, rhodamine, and the like. Chemiluminescent markers are, for example, acridinium esters or luminol. In such conjugates the antibodies are bound to the enzymes or markers directly or by the way of a spacer or linker group. Examples for metal chelators are ethylenediamintetraacetic acid (EDTA), diethylenetriaminepentaacetic acid (DPTA), 1,4,8,11-tetraazatetradecane, 1,4,8,11-tetraazatetradecane-1,4,8,11-tetraacetic acid, 1-oxa-4,7,12,15-tetraazaheptadecane-4,7,12,15-tetraacetic acid, or the like.

Radioactively labelled monoclonal antibodies contain e.g. radioactive iodine ($^{123}$I, $^{125}$I, $^{131}$I), yttrium ($^{90}$Y), technetium ($^{99m}$Tc), or the like.

Antibody fragments of the invention are for example the univalent fragments Fab (Fab=fragment antigen binding) or Fab' and the divalent fragment F(ab')$_2$.

Monoclonal antibodies and derivatives thereof according to the invention are prepared by processes that are known per se, characterized in that hybridoma cells as defined above secreting birudin-specific monoclonal antibodies are multiplied according to known methods in vitro or in vivo. When required, the resulting monoclonal antibodies are isolated and/or converted into derivatives thereof.

Multiplication in vitro is carried out in suitable culture media, which are the customary standard culture media, for example Dulbecco's Modified Eagle Medium (DMEM) or RPMI 1640 medium, optionally replenished by a mammalian serum, e.g. foetal calf serum, or trace elements and growthsustaining supplements, e.g. feeder cells such as normal mouse peritoneal exudate cells, spleen cells, bone marrow macrophages, or the like.

In vitro production provides relatively pure antibody preparations and allows scale-up to give large amounts of the desired antibodies. Techniques for large scale hybridoma cultivation under tissue culture conditions are known in the art and include homogeneous suspension culture, e.g. in an airlift reactor or in a continuous stirrer reactor, or immobilized or entrapped cell culture, e.g. in hollow fibres, microcapsules, on agarose microbeads or ceramic cartridges.

For isolation of the monoclonal antibodies, the immunoglobulins in the culture supernatants are first concentrated e.g. by precipitation with ammonium sulphate, dialysis against hygroscopic material such as PEG, filtration through selective membranes or the like. If necessary and/or desired, the concentrated antibodies are purified by customary chromatography methods, for instance gel filtration, ion exchange chromatography, chromatography over DEAE-cellulose or Protein A, or immunoaffinity chromatography.

Large amounts of the desired monoclonal antibodies can also be obtained by multiplying hybridoma cells in vivo. Cell clones are injected into mammals which are histocompatible with the parent cells, e.g. syngeneic mice, to cause growth of antibody-producing tumors. Optionally, the animals are primed with a hydrocarbon, especially mineral oils such as pristane (tetramethylpentadecane), prior to the injection. As an example, hybridoma cells derived from Balb/c mice are intraperitoneally injected into Balb/c mice optionally pretreated with pristane, and after one to two weeks ascites fluid of these mice is collected. The desired monoclonal antibodies are isolated from the body fluids by conventional methods as described above.

Conjugates of monoclonal antibodies of the invention are prepared by methods known in the art, e.g. by reacting a monoclonal antibody prepared as described hereinbefore with an enzyme in the presence of a coupling agent, e.g. glutaraldehyde, periodate, N,N'-o-phenylenedimaleimide, N-(m-maleimidobenzoyloxy)-succinimide, N-(3-[2'-pyridyldithiol-propionoxy)-succinimide, N-ethyl-N'-(3-dimethylaminopropyl)-carbodiimide or the like. Conjugates with avidin are prepared likewise. Conjugates with biotin are prepared e.g. by reacting monoclonal antibodies with an activated ester of biotin such as the biotin N-hydroxysuccinimide ester. Conjugates with fluorescent markers are prepared in the presence of a coupling agent, e.g. those listed above, or by reaction with an isothiocyanate, preferably fluorescein-isothiocyanate. Antibody-conjugates with metal chelates are prepared in an analogous manner. Conjugates with chemiluminescent markers, e.g. acridinium esters, are prepared by reacting monoclonal antibodies with the markers in activated form, e.g. active ester derivatives.

Monoclonal antibodies radioactively labelled with iodine ($^{123}$I, $^{125}$I, $^{131}$I) are obtained from the monoclonal antibodies according to the invention by iodination known per se, for example with radioactive sodium or potassium iodide and a chemical oxidising agent, such as sodium hypochlorite, chloramine T or the like, or an enzymatic oxidising agent, such as lactoperoxidase, glucose oxidase and glucose. Monoclonal antibodies according to the invention are coupled to yttrium ($^{90}$Y) for example by diethylene-triaminepentaacetic acid (DPTA)-chelation. Technetium-99m labelled antibodies are prepared by ligand exchange processes, for example by reducing pertechnate (TcO$_4^-$) with stannous solution, chelating the reduced technetium onto a Sephadex column and applying the antibody to this column, or by direct labelling techniques, e.g. by incubating pertechnate, a reducing agent such as SnCl$_2$, a buffer solution such as a sodium-potassium phthalate-solution, and the antibody.

Fragments of monoclonal antibodies, for example Fab, Fab' or F(ab')$_2$ fragments, which retain their specifity towards hirudin, can be obtained from the antiantibodies prepared as described above by methods known per se, e.g. by digestion with enzymes such as pepsin or papain and/or cleavage of disulfide bonds by chemical reduction.

The monoclonal antibodies and derivatives thereof according to the invention are useful for the qualitative and quantitative determination of hirudin.

For instance, the monoclonal antibodies or derivatives thereof can be used in any of the known immunoassays which rely on the binding interaction between the antigenic determinants of the hirudin molecule and the paratopes of the monoclonal antibodies, such as radioimmunoassays (RIA), enzyme immunoassays, immunofluorescence tests, latex agglutination or haemagglutination, chemiluminescence, laser light scattering, or evanescent light tests.

The monoclonal antibodies of the invention can be used as such or in the form of radioactively labelled derivatives in a radio immunoassay (RIA). Any of the known modifications of a RIA can be used, for example soluble phase (homogeneous) RIA, solid phase (heterogeneous) RIA, single RIA or double (sandwich) RIA with direct or indirect (competitive) determination of hirudin. Preferred is a sandwich RIA in which a suitable carrier, for example the plastics surface of a microtiter plate or of a test tube, e.g. of polystyrene, polypropylene or polyvinyl chloride, glass or plastic beads, filter paper, dextran etc., cellulose acetate or nitrocellulose sheets, magnetic particles, or the like, is coated with a monoclonal antibody specific for hirudin, preferentially the monoclonal antibody MAb 4049-83-12. Then test solutions containing hirudin and finally polyclonal antibodies, which also react with the antigen, for example sheep anti-hirudin polyclonal antibodies, and which are radioactively labelled, e.g. with $^{125}$I, are added. The amount of hirudin in the test solution is directly proportional to the amount of bound polyclonal antibodies and is determined by measuring the radioactivity bound to the carrier. The polyclonal antibodies can be replaced by a second radioactively labelled monoclonal antibody of the invention which recognizes a different epitope of hirudin than the first carrier-bound monoclonal antibody.

The monoclonal antibodies according to the invention can be used as such or in the form of enzyme-conjugated derivatives in an enzyme-immunoassay. Such immunoassays include test procedures in which enzyme-labelled monoclonal antibody derivatives according to the invention or enzyme-labelled antibodies known per se that recognize and bind an epitope of the antibodies of the invention are used.

There is preferred an enzyme-linked immunosorbent assay (ELISA) in which a carrier as described above for a RIA is coated with a monoclonal antibody of the invention, preferentially MAb 4049-83-12, incubated with test solutions containing hirudin, with polyclonal antibodies as described above which are enzyme-conjugated and with a substrate solution. The enzyme substrate reaction results, for example, in a colour change and can be observed by eye or with optical measuring devices, so that the amount of bound enzyme, which is proportional to the amount of hirudin in the test solution, can be determined. The polyclonal antibodies can be replaced by a second enzyme-conjugated monoclonal antibody of the invention which recognizes a different epitope of hirudin than the first carrier-bound monoclonal antibody. There is also preferred an ELISA in which the carrier is coated with a monoclonal antibody according to the invention, preferentially the monoclonal antibody MAb 4049-83-12, incubated with a test solution containing hirudin and then with the polyclonal serum as described above and, finally, the bound antibodies of the polyclonal serum are developed by enzyme-labelled antibodies that recognize and bind to them, and the amount of the protein bound is determined by an enzyme substrate reaction as hereinbefore described. Such enzyme-labelled antibodies are, for example, phosphatase-labelled goat anti-sheep immunoglobulins.

Also preferred is an enzyme immunoassay called immunodot analysis, in which test or standard solutions containing hirudin are spotted on a microporous carrier with high intrinsic affinity for polypeptides, e.g. on nitrocellulose, the carrier bearing one or several dots of said samples is incubated in a solution of a monoclonal antibody of the invention, preferentially the monoclonal antibody MAb 4049-83-12, then in a solution of an enzyme-labelled second antibody that recognizes and binds the monoclonal antibody of the invention and finally in a solution of an enzyme substrate which leads to a detectable signal, e.g. a coloured substance. Such an enzyme-labelled second antibody is e.g. rabbit anti-mouse immunoglobulin conjugated with horseradish peroxidase which can be developed with suitable enzyme substrates such as 4-chloro-1-naphthol or the like.

The monoclonal antibodies according to the invention can be used as such or in the form of derivatives according to the invention conjugated with fluorescent markers in immunofluorescence tests. Such immunnofluorescent tests include procedures wherein monoclonal antibody derivatives according to the invention, e.g. derivatives conjugated with fluorescein, or fluorescent marker-labelled antibodies known per se that recognize and bind an epitope of the monoclonal antibody of the invention are used.

In an analogous manner, the monoclonal antibodies of the invention can be used as such or in form of derivatives according to the invention conjugated with chemiluminescent markers in immunochemiluminescence tests.

The use according to the invention of monoclonal antibodies and derivatives thereof as described hereinbefore for the qualitative and quantitative determination of hirudin also includes other immunoassays known per se, for example latex agglutination with antibody-coated or antigen-coated latex particles, hemagglutination with antibody-coated or antigen-coated red blood corpuscles, evanescent light wave assays using an antibody-coated optical fibre and other direct-acting immunosensors which convert the binding event into an electrical or optical signal, or the like.

The application of the monoclonal antibodies of the invention and/or derivatives thereof in the above-described assays allows the determination of the presence and/or the concentration of hirudin in buffer, urine and plasma. In buffer and plasma, hirudin can be determined in concentrations ranging from 0.1 to 100 ng/ml. The assays can be used e.g. to assess the pharmacokinetics of hirudin in patients after the parenteral and/or topic administration, also for the detection of bacterial strains that express the cloned hirudin gene and for following the various purification steps when hirudin is isolated from leeches or transformed bacteria.

The present invention also concerns the use of the monoclonal antibodies of the invention, preferentially of MAb 4049-83-12 or MAb 4120-37-7, which neutralize the anticoagulation activity and derivatives thereof as an antidote to hirudin, that is to say that the excess anticoagulation effect of a hirudin overdose can be normalized by addition of these antibodies irrespective of the degree of anticoagulation achieved. Thus, the antithrombotic effect of hirudin will be balanced. The therapeutic dose for mammals is between approximately 1 and 10 mg per kg body weight for monoclonal antibodies themselves, and between 0.1 and 10 mg for antibody derivatives, depending on the status of the patient and the mode of application.

The antidote activity of the monoclonal antibodies of the invention and derivatives thereof can be measured by conventional tests known in the art, for example by the coagulation assay of Fenton & Fasco (Thrombosis Res. 4, 809, 1974) in which different concentrations of a monoclonal antibody of the invention are incubated with hirudin, thrombin and fibrinogen, and the clotting time is measured. Assays employing chromogenic substrates, which measure the cleavage of the chromogene by α-thrombin, are also suitable for measuring the antidote activity.

The invention also concerns test kits for the qualitative and quantitative determination of hirudin comprising monoclonal antibodies of the invention and/or derivatives thereof and, optionally, other monoclonal or polyclonal antibodies and/or adjuncts.

Test kits according to the invention for a radioimmunoassay contain, for example, a suitable carrier, uncoated or coated with a monoclonal antibody of the invention, optionally freeze-dried or concentrated solutions of a monoclonal or polyclonal antibody specific for hirudin and/or a radiolabelled derivative thereof, standard hirudin-solutions, buffer solutions and, optionally, polypeptides and detergents for preventing non-specific adsorption and aggregate formation, pipettes, reaction vessels, calibration curves, instruction manuals and the like.

Test kits according to the invention for an enzyme immunoassay contain, for example, a suitable carrier, e.g. microtiter plates or nitrocellulose sheets, optionally freeze-dried or concentrated solutions of a monoclonal antibody of the invention and of an enzyme-labelled monoclonal or polyclonal antibody specific for hirudin or to a first antibody recognizing hirudin, enzyme substrates in solid or dissolved form, standard hirudin-solutions, buffer solutions and, optionally, polypeptides and detergents, pipettes, reaction vessels, calibration curves, colour scale tables, instruction manuals and the like.

The invention also concerns pharmaceutical preparations comprising monoclonal antibodies specific for hirudin according to the invention which neutralize the anticoagulation activity of hirudin and/or derivatives thereof in a therapeutically effective amount together or in admixture with solid or liquid, organic or inorganic pharmaceutical carriers.

Preferred are pharmaceutical preparations for parenteral application. Preparations for intramuscular, subcutaneous or intravenous application are e.g. isotonic aqueous solutions or suspensions, optionally prepared shortly before use from lyophilized or concentrated preparations. The pharmaceutical preparations may be sterilized and contain adjuvants e.g. for conserving, stabilizing, wetting, emulsifying or solubilizing the ingredients, salts for the regulation of the osmotic pressure, buffer and/or compounds regulating the viscosity, e.g. sodium carboxycellulose, dextran, polyvinylpyrrolidone or gelatine. They are prepared by methods known in the art, e.g. by conventional mixing, dissolving or lyophilizing, and contain from approximately 0.01% to approximately 50% of active ingredients. The preparations for injections are processed, filled into ampoules or vials, and sealed under aseptic conditions according to methods known in the art.

BRIEF DESCRIPTION OF THE FIGURES

In FIG. 1, the concentration of inhibitor (ng/ml) is plotted against the percentage of MAb bound to the microtiter plate (B/Bo×100%). Symbols: MAb 4049-83-12 with (*) rHV1 or with ( ) rHV1 peptide 52–65; MAb 4102-21-14 with (triangles) rHV1 or with (squares) rHV1 peptide 52–65.

In FIG. 2, the concentration of MAb (pg/ml) is plotted against the clotting time (sec).
Symbols:
(≠) MAb 4049-83-12); (triangles) RAb 4114-96-1;
(○) MAb 4120-37-7; (squares) MAb 4102-21-14; (*) MAb 4049-83-12 without rHV1.

Figure 1:
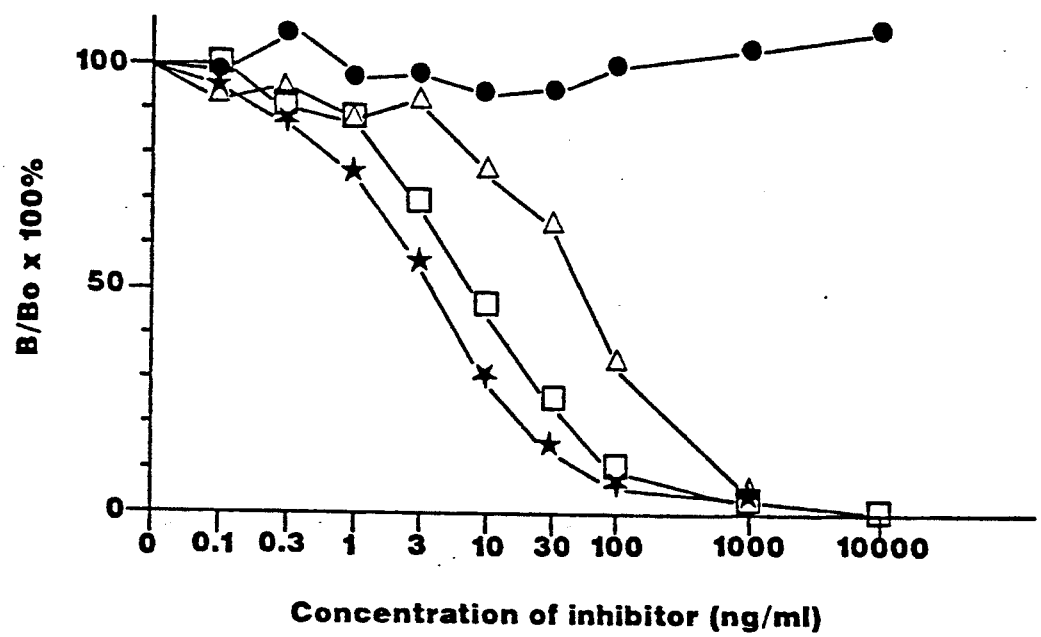
FIG. 1: Competitive ELISA (see example 4.5)

The following examples illustrate the invention, but do not limit it to any extent.

Abbreviations

HAT—hypoxanthine/aminopterin/thymidine
HPLC—high pressure liquid chromatography
MES—2-[N-morpholino]ethane-sulfonic acid
PBS—phosphate buffered saline
PEG—polyethylene gylcol
rHV1—recombinant hirudin variant HV1
RT—room temperature

EXAMPLES

Example 1: Preparation of anti-hirudin monoclonal antibodies 1.1 Preparation of various immunogens 1.1.1 Coupling of r-hirudin variant HV1 to a carrier protein Recombinant hirudin variant HV1 (rHV1; Plantorgan/Ciba-Geigy) is coupled to bovine serum albumin (BSA, Fluka) by the carbodiimide method after protecting the $NH_2$ groups of rHV1 by di-tert.-butyl-dicarbonate (t-$(BOC)_2O$, Fluka) to avoid hirudin-hirudin crosslinking. Since the hirudin C-terminal domain is very rich in acidic residues which are exposed on the surface of the hirudin molecule (Chang, FEBS Lett. 164, 307, 1983), it is assumed that the carbodiimide coupling (after protection of the hirudin amino groups) should mainly link the hirudin by its C-terminal domain to the carrier protein and therefore should preferentially trigger an immune response against the N-terminal domain of hirudin.

The coupling procedure is carried out as follows:
To 1 mg of rHV1 in 20 μl of $H_2O$ 5 μl of triethylamine 0.4M, 50 μl of N,N-dimethyl-formamide and 2 μl of t-$(BOC)_2O$ are added. After 2 hours at 37° C., 50 μl of $H_2O$ and 200 μl of ethyl acetate are added to extract the unreacted t-$(BOC)_2O$. The extraction is repeated twice. The lower phase is dried out and 250 μl of 0.1M MES buffer (pH 4.75) are added together with 50 μl of BSA (10 mg/ml) and 100 μl N-ethyl-N'-(3-dimethylamino-propyl)-carbodiimide hydrochloride (20 mg/ml). After 2 h at RT, the mixture is dried out and 200 μl of tri-fluoro-acetic acid (TFA) 90% are added to deprotect the amino groups after coupling. After 10 min at RT, the TFA is evaporated, and 1 ml of PBS (8.5 g NaCl, 1.28 g $Na_2HPO_4.2H_2O$, 0.436 g $NaH_2PO_4.2H_2O$ ad 1000 ml $H_2O$) is added. The solution is extensively dialyzed in PBS before using it for immunization.

The extent of protection of the amino groups of rHV1 by t-$(BOC)_2O$ is assessed by reverse-phase HPLC. The treated rHV1 elutes mainly in one peak with a retention time superior to untreated rHV1. The presence of mainly one peak suggests that the protection of rHV1 amino groups is comparable for all molecules. Indeed, addition of more t-$(BOC)_2O$ with concomitant extension of the reaction time has no effect on the elution profile, suggesting that the reaction is already completed.

After deprotecting the amino groups by TFA treatment and after extensive dialysis, the conjugate is analyzed by SDS-PAGE (sodium dodecyl sulfate polyacrylamide gel electrophoresis). The coupling of rHV1 to BSA is evidenced by a diffuse band migrating slower than BSA.

1.1.2 Coupling of rHV1 peptides to a carrier protein

Synthetic peptides representing amino acids 40–65 and 52–65, respectively, of rHV1 (referred to as rHV1 peptide 40–65 and 52–65, respectively) are synthesized by methods known in the art (Rink, Tetrahydron Letters 28, 3787, 1987). 1 mg of each rHV1 peptide in 50 ml $H_2O$ is added to 5 mg of KLH (keyhole limpet haemocyanin, Calbiochem) in 500 ml PBS. 20 μl glutaraldehyde 25% (Fluka) are then added and the mixture is incubated for 2 h at RT. Then 50 μl of L-lysine (100 mg/ml) are added to stop the reaction.

The thrombin inhibiting action of C-terminal hirudin HV1 and HV3 peptides has been shown e.g. by Mao et al. (Biochemistry 27, 8170, 1988) and Krstenansky et al. (Thromb. Res. 52, 137, 1988). The minimal C-terminal amino acid residues necessary for thrombin inhibiting activity are 56–65.

1.2 Immunization with the various immunogens

Four groups of five Balb/c female mice (4–6 weeks old) are given three series of injections with respectively, (group I) BSA-conjugated rHV1 (15 μg/injection), (group II) KLH-conjugated rHV1 peptide 40–65 (10 μg/injection), (group III) KLH-conjugated rHV1 peptide 52–65 (10 μg/injection), and (group IV) native rHV1 (uncoupled, in adjuvant) (50 μg/injection). The first injection consists of 0.1 ml of the respective immunogen in PBS mixed in a 1:1 ratio with 0.1 ml of complete Freund's adjuvant (Difco); 50 μl are injected intraperitoneally and 150 μl subcutaneously. In the second (day 14) and third (day 30) series of injections, complete Freund's adjuvant is replaced by incomplete Freund's adjuvant. One week after the last injection, serum is collected and antibody titers are determined by an enzyme-linked immunosorbent assay (ELISA) as described in examples 1.3.1 and 1.5.

1.3 Assays for testing of the various sera

1.3.1 Sandwich enzyme-linked immunosorbent assay (ELISA) for determination of antibody serum titer The antibody titer in the various sera is determined one week after the last immunization in an indirect ELISA using rHV1 to coat the microtiter plates as described in example 1.5. Instead of diluted hybridoma supernatants, 100 μl of the respective serum diluted in PBS-Tween 0.1 % are added to the microtiter wells coated with the antigen. As control, the antibody titer of the sera before immunization (preimmune sera) is determined.

The serum titers, i.e. the last serum dilution giving a signal three times above the control (preimmune sera), are:

| | |
|---|---|
| group I (BSA-rHV1): | $1 \times 10^6$ |
| group II (KLH-rHV1 peptide 40-65): | $1 \times 10^5$ |
| group III (KLH-rHV1 peptide 52-65): | $3 \times 10^5$ |
| group IV (native rHV1): | $3 \times 10^4$. |

The highest titer is obtained using rHV1 coupled to BSA as immunogen, whereas uncoupled rHV1 gives a very low immune response.

1.3.2 Competitive ELISA for determination of cross-inhibition

The competitive ELISA employed for the determination of cross-inhibition in the sera is described below in example 4.5. Instead of purified MAb, however, 50 μl of the respective serum, diluted 1:2000 (groups I and III), 1:1500 (group II) and 1:200 (group IV), in PBS-Tween 0.1% are used.

The resulting $IC_{50}$ values, i.e. the concentration of the compound used for preincubation (rHV1, rHV1 peptide 52–65 or rHV3) necessary to inhibit 50 % of the binding of the serum antibodies to the plates, are given in Table 2.

TABLE 2

| | Competitive ELISA for determination of cross-inhibition in the sera | | | |
|---|---|---|---|---|
| | $IC_{50}$ (ng/ml) | | | |
| compound used for preincubation | group I (BSA-rHV1) | group II (KLH-rHV1 peptide 40-65) | group III (KLH-rHV1 peptide 52-65) | group IV (native rHV1) |
| rHV1 | 3.5 | 39 | 23 | 30 |
| rHV1 peptide 52-65 | >1000 | 97 | 11 | >1000 |
| rHV3 | >1000 | >1000 | >1000 | >1000 |

In the competitive ELISA assay, all sera bind rHV1 in solution. Sera of mice immunized with the synthetic rHV1 peptide 52–65 or 40–65 cross-react with native rHV1, suggesting that the determinants recognized by the rHV1 peptide antisera are readily accessible in a correct conformation on the native molecule. These data confirm previous observations showing that the C-terminal segment is exposed on the surface of the hirudin molecule (Chang, FEBS Lett. 164, 307, 1983). On the other hand, only mice immunized with the C-terminal rHV1 peptides (groups II and III) have sera which can be inhibited 100% by the rHV1 peptide 52–65, whereas sera of mice immunized with the whole molecule (groups I and IV) do not crossreact.

1.3.3 Coagulation assay for determination of neutralizing activity

The coagulation assay employed to determine the ability of the various sera to neutralize the anticoagulation activity of hirudin is described below in example 8. Instead of purified MAb, mouse sera diluted 1:10 or 1:100 are incubated with rHV1.

The results are given in Table 3 as the multiple of clotting time, i.e. the ratio of clotting time in the presence of rHV1 to clotting time in the absence of rHV1.

TABLE 3

| | Neutralizing capacity of the sera multiple of clotting time | | | | |
|---|---|---|---|---|---|
| serum dilution | group I (BSA-rHV1) | group II (KLH-rHV1 peptide 40-65) | group III (KLH-rHV1 peptide 52-65) | group IV (native rHV1) | control (preimmune serum) |
| 1:10 | 1.0 | >7* | >7 | 3.1 | >7 |
| 1:100 | 2.3 | >7 | >7 | >7 | nd | nd — not determined
*clotting time in the presence of rHV1 >180 s (unclottable)

The sera show drastic differences in their capacity to neutralize the anti-coagulation activity of rHV1 towards thrombin. Only sera of mice from group I show complete neutralizing capacity, whereas the other sera have low (group IV) or no (groups II, III) neutralizing activity. Due to the low serum titers of mice of group IV, only mice of groups I, II, and III are selected for the production of MAbs.

1.4 Fusion protocol

After a rest period of two months, the mice are boosted intraperitoneally with either 75 μg of BSA-rHV1-conjugate (group I) or 80 μg of the KLH-rHV1 peptide conjugates (groups II and III) in PBS (200 μl). Three to four days later, the mice are sacrificed, the spleen cells are fused with the murine myeloma cell lines Sp2/0-Ag14 (Shulman et al., Nature 176, 269, 1978) or PAI (Stocker et al., Hoffmann-LaRoche Research Disclosure No. 21713, 1982), using PEG 4000 (Merck), by a modification of the original Koehler and Milstein method (Galfre et al., Nature 266, 550, 1977), and the cells are distributed into microtiter plate wells containing HAT medium (Boehringer). After 2 to 4 weeks, wells containing growing hybridomas are tested for specific monoclonal antibodies by ELISA as described in example 1.5.

1.5 Hybridoma screening by an indirect enzyme-linked immunosorbent assay (ELISA)

The growing hybridomas are tested for the presence of anti-hirudin antibodies by an indirect enzyme-linked immunosorbent assay (ELISA).

Microtiter plates (Dynatech) are coated with 100 μl per well of a solution of either (i) rHV1 (3 pg/ml) in coating buffer (50 mM sodium carbonate buffer pH 9.6:477 mg $Na_2CO_3$, 879 mg $NaHCO_3$, 1.8 ml $NaN_3$, 0.5M, ad 300 ml $H_2O$) or (ii) biotinylated rHV1 (5 pg/ml) complexed with avidin (10 μg/ml) (see example 4.1) in coating buffer. The additional coating using rHV1 linked to a carrier molecule is developed to avoid conformational changes of the hirudin molecule after its adsorption onto the plastic well. The plates are incubated overnight at 4° C. in a moist chamber and washed five times with PBS-Tween 0.1% (1 ml Tween-20, Serva, 1000 ml PBS). The wells are allowed to dry, filled with 200 ml per well of PBS-BSA 1% (1 g BSA, 3 ml $NaN_3$0.5M, ad 100 ml PBS), incubated for 2 h at RT and washed five times with PBS-Tween 0.1%. Then, 200 μl of hybridoma cell supernatants diluted 1:2 in PBS-Tween 0.1% are added to each well. After 2 h incubation at RT, the plates are washed five times with PBS-Tween 0.1%. In the next step, 100 μl of alkaline phosphatase affinity purified goat antibody to mouse IgG (Kirkegaard & Perry Laboratories) diluted 1:1500 in PBS-Tween 0.1% are added to each well. The plates are incubated for 1.5 h at RT and are washed five times with PBS-Tween 0.1 %. Finally, 150 μl per well of substrate solution (1 mg p-nitrophenylphosphate [Sigma] per ml diethanolamine buffer pH 9.8:97 ml diethanolamine [Merck], 6 ml $NaN_3$0.5M, 100 mg $MgCl_2.6H_2O$, adjusted to pH 9.8 with HCl conc., ad 1000 ml $H_2O$) are added, the reaction is stopped by adding 50 μl of NaOH 3M, and the optical density is read at 405 nm after 2 h incubation at RT in the dark.

Four hybridoma cell lines secreting anti-hirudin monoclonal antibodies are selected for further studies due to their high affinity for hirudin within their groups and have been deposited at the European Collection of Animal Cell Cultures (ECACC). The designations and deposition numbers are given in Table 4.

TABLE 4

| | Hybridomas secreting anti-hirudin MAbs | | |
|---|---|---|---|
| hybridoma designation | obtained from a mouse of | deposition number (ECACC) | deposition date |
| 4049-83-12 | group I | 8808 2504 | August, 25, 1988 |
| 4114-96-1 | group II | 8903 2102 | March 21, 1989 |
| 4120-37-7 | group II | 8903 2103 | March 21, 1989 |
| 4102-21-14 | group III | 8903 2101 | March 21, 1989 |

The monoclonal antibodies secreted by these hybridomas are designated by the prefix "MAb" and the number of the respective hybridoma, e.g. MAb 4049-83-12.

1.6 Hybridoma storage and processing

The selected hybridoma cells can be grown in culture, frozen at −800° C. and kept in liquid nitrogen and then reactivated. The cells are cloned by the method of limiting dilution (Goding, J. Immunol. Methods 39, 285, 1980) and expanded by forming ascites in Balb/c mice primed with pristane (see example 2.1).

Example 2: Production, isolation and purification of the anti-hirudin monoclonal antibodies

2.1 Expansion of hybridomas in vivo and purification of the monoclonal antibodies For ascites production, female Balb/c mice (20–25 g) (Tierfarm Sisseln, Switzerland) are pretreated with 0.3 ml pristane oil (Aldrich) intraperitoneally. 1 to 3 weeks later, the mice receive a second injection of pristane (0.2 ml i.p.) and are simultaneously inoculated i.p. with $2 \times 10^6$ hybridoma cells in 0.2 ml PBS. After 8–10 days, the resulting ascites fluid is collected, centrifugated at 800 g and stored at $-20°$ C. or at $-80°$ C.

Defrosted ascites fluid is clarified by centrifugation at 30,000 g for 1 h. After removing the top layer containing lipids, the protein concentration is determined and adjusted to 10–12 mg/ml with PBS. The immunoglobulin G fraction (IgG) is precipitated by dropwise addition of 0.9 volumes of saturated ammonium sulfate at $0°$ C. After 1 h, the IgG fraction is pelleted by centrifugation for 1 h at 22,000 g. The pellet is dissolved in 20 mM Tris-HCl buffer pH 7.9 containing 50 mM NaCl, and is dialyzed against the same buffer overnight at $40°$ C. The IgG fraction is further purified by anion exchange chromatography on a column of DE52 diethylaminoethyl cellulose (Whatman). The sample is diluted 1:2 (v/v) in 20 mM Tris-HCl pH 7.9 to a final concentration of 25 mM NaCl, and 10 mg of protein per ml of gel are loaded onto the column. The elution is obtained by increasing the sodium chloride concentration from 25 mM to 200 mM (linear gradient). In general, MAbs are eluted around 80 mM NaCl. The fractions are dialyzed against PBS overnight at $40°$ C. and stored at $-70°$ C. Purity is assessed by SDS-PAGE and isoelectric focusing. Puritiy is more than 90%.

2.2 Expansion of hybridomas in vitro

A preculture of any of the cell lines is obtained by culturing hybridoma cells at physiological temperature (around $37°$ C.) in RPMI 1640 medium (Seromed) containing 10% foetal calf serum (FCS) to a final cell density of $5 \times 10^5$ to $10^6$ cells per ml. The whole preculture is filled into Bellco culture vessels and adjusted to a total volume of 1500 ml with fresh RPMI 1640 medium/10% FCS. The culture is stirred at around $37°$ C. under 5% $CO_2$ at 30 rpm for two to three days, then diluted to a total volume of 3000 ml with RPMI 1640/10% FCS and stirred for another seven to ten days. After this time 95% of the cells are dead. The culture broth is centrifuged at $1000 \times g$ for 20 min at $40°$ C. The supernatant is filtered through a filter with pore size 0.2 μm under sterile conditions. Crude immunoglobulin is precipitated by slow dropwise addition of 0.9 volume equivalents of saturated ammonium sulfate at $0°$ C. This precipitate is purified as described in Example 2.1.

Example 3: Determination of class and subclass of the anti-hirudin monoclonal antibodies The class and subclass of the anti-hirudin monoclonal antibodies is determined in an enzyme-linked immunosorbent assay (ELISA) kit from Bio-Rad. The monoclonal antibodies MAb 4049-83-12, MAb 4114-96-1 and MAb 4102-21-14 are of class IgG1, and MAb 4120-37-7 is of class Ig G2b.

Example 4: Determination of epitopes recognized by the anti-hirudin monoclonal antibodies The hirudin epitope(s) recognized by the anti-hirudin monoclonal antibodies are mapped (i) by competitive ELISA experiments using rHV1, rHV1 analogues and recombinant hirudin variant PA (rHV3), and (ii) by proteolysis of the antigen-antibody complex.

4.1 Preparation and characterization of biotinylated rHV1 rHV1 is first biotinylated with biotin-X-N-bydroxysuccinimide ester using a low molar ratio of biotin to rHV1 and then linked to avidin in the procedure described below.

0.5 mg rHV1 in 200 μl of acetate buffer (20 mM, pH 6.0) are mixed with 100 μg of biotin-X-N-hydroxysuccinimide ester (Calbiochem) dissolved in 40 μl ethanol/water (1:1, v/v) so that the molar ratio of biotin to rHV1 is 3.2:1, and the mixture is incubated 20 min at RT. Then, 260 μl of PBS are added and the solution is dialyzed overnight against PBS at $4°$ C.

The chromatography of the biotinylated rHV1 by reverse-phase HPLC reveals several peaks in addition to the one corresponding to unmodified rHV1. Such an heterogeneity is indeed expected due to the low ratio of biotin to hirudin used, which should favour the derivatization of only a portion of the four amino groups available per molecule for modification.

The extent of biotinylation of each amino group is further quantitatively determined by digestion of modified and unmodified rHV1 by trypsin (Worthington) or by lysyl endopeptidase from *Acbromobacter lyticus* (Wako) after reductive S-carboxymethylation (Hirs, Methods in Enzymol. 11, 199, 1967) (S-CM-rHV1), and by separation of the fragments by reverse phase HPLC. Briefly, 0.1 mg of biotinylated rHV1 (or rHV1 ) is diluted in 200 μl Tris buffer 0.5M, pH 8.4, supplemented with 5M guanidine-chloride and 2 mM EDTA (RM Buffer). The solution is heated at $50°$ C. for 30 min and then cooled down to $37°$ C. 1 mg of DL-dithiothreitol (DDT) in 100 μl RM buffer is added, and the mixture is incubated 2 h at $37°$ C. After cooling to RT, 2 mg of iodoacetic acid in 100 μl RM buffer are added and the mixture is further incubated for 30 min at RT. The excess of reagent is removed by gel filtration on a G25 Sephadex column (Pharmacia) using $(NH_4)HCO_3$ 50 mM, pH 8.0, as elution buffer. The fractions containing the carboxymethylated rHV1 are then subjected either to trypsin digestion (by adding L-1-p-tosylamido-2-phenylethylcbloromethylketone-trypsin, Worthington), or to lysyl endopeptidase digestion. The ratio of trypsin or lysyl endopeptidase to rHV1 is 1 to 50 (w/w) and 1 to 10 (w/w), respectively. After 3 h at $37°$ C., the same amount of enzyme is added again and the incubation is carried out for another 3 h period. The reaction is stopped by freezing the mixture at $-20°$ C. The separation of the proteolytic fragments (1–2 pg) is done by HPLC on a C-18 column. The gradient is as follows: solvent A, 0.1% (v/v) anhydrous trifluoroacetic acid (TFA) in water, and solvent B, 0.1% (v/v) anhydrous trifluoroacetic acid in acetonitrile. Elution is with a linear gradient, with solvent B increasing from 30 to 80% in 33 min. The flow rate is 1 ml/min. Peptides are detected by measuring the absorbance at 210 nm. The identification of peptides is done by amino-terminal analysis as described previously (Chang, Analytical Biochem. 170, 542, 1988).

By assuming that the extent of modification is directly correlated with the extent of disappearance of each tryptic fragment, the percentage of modification is calculated from the decrease in area of each peak from modified rHV1 relative to unmodified rHV1. These data are further confirmed by quantitative amino-terminal analysis of the tryptic digest (i.e. without HPLC separation of the tryptic fragment). The N-terminal amino acids Val 1, Lys 27 and Lys 36 are well modified in an extent between 30% and 50%. Lysyl endopeptidase, which cleaves the amide bond between Lys 47 and Pro 48 (that is not cleaved by trypsin), allows determination of the extent of modification of Lys 47. The latter is between 30% and 40%.

4.2 Preparation of acetylated, succinylated, S-DABITC and S-DAB-diazonium rHV1

Acetylation and succinylation of the amino groups of rHV1 is carried out by adding to 140 nmol of rHV1 in 1 ml sodium bicarbonate buffer (0.1M pH 8.5) either 140 μmol of succinic anhydride or of acetic anhydride. After 30 min at RT, the reaction is blocked by addition of L-lysine (2 mg), and the mixture is dialyzed against PBS.

Derivatization of rHV1 with S-DABITC (4-N,N-dimethylaminoazobenzene-4'-isothiocyanate-2'-sulfonic acid) is done as follows: rHV1 (2 mg, freeze-dried) is dissolved in 1 ml of S-DABITC solution (1 mM in 50 mM sodium bicarbonate solution, pH 8.3). Derivatization is carried out at 37° C. A 200 μl (400 μg) aliquot is withdrawn at time intervals of 30 min, 1.5 h, 4 h and 7 h, and immediately passed through a disposable G-25 column (PD-10 from Pharmacia, equilibrated with 50 mM ammonium bicarbonate) in order to remove the excess reagent. Derivatized rHV1 is visible during gel filtration, and 1.3 to 1.4 ml are collected without the aid of a detector. Absorbance (465 nm) of the collected solution is recorded, and the extent of modification (moles of S-DABITC per mole of rHV1) is calculated based on the molar extinction coefficient of the S-DABITC group as 28,000 (Chang, J. Biol. Chem. 264, 3111, 1989).

S-DAB-diazonium is synthesized as follows: 20 mg of 4-dimethylamino-4'-aminoazobenzene-2'-sulfonic acid are solubilized in 1 ml of water containing 8 mg of sodium carbonate. The solution is put on ice, and 6 mg of $NaNO_2$ in 100 μl of water are then added. The mixture is mixed with 300 μl of cold HCl 4N and stirred on ice for 30 to 45 min. The pH of the mixture is adjusted to pH 5.0 using NaOH 5 N. The diazonium derivative is stored at −20° C. in the dark. The modification of rHV1 (200 pg in 390 μl sodium carbonate buffer pH 8.8, 0.67M) is done by adding 650 nmol of S-DAB-diazonium. After 3 h incubation on ice, the excess of reagent is eliminated by gel filtration (see above). The quantitative determination of the extent of modification of the reactive residues of hirudin by S-DABITC or by S-DAB-diazonium is performed by V8 proteolysis after reductive S-carboxymethylation of the modified hirudin (see above). The fragments are separated by HPLC, and those containing modified residues are detected by absorbance at 450 nm. They are collected and identified by amino-acid sequencing.

4.3 Digestion of rHV1 by V8 staphylococcal protease 70 pg of native rHV1 dissolved in 90 pl of $(NH_4)HCO_3$ buffer 50 mM, pH 8.0, supplemented with EDTA 2 mM, are mixed with 20 μg (in 20 μl) of *Staphylococcus aureus* strain V8 protease (Sigma), and incubated for either 30 min, 2 h or 4 h at 37° C. The reaction is stopped by the addition of 5 μl of diisopropylfluorophosphate 0.01M (Sigma). The extent of digestion is assessed by reverse-phase HPLC (see example 4.6), or by amino-terminal analysis (Chang, Analytical Biochem. 170, 542, 1988), and by SDS-PAGE.

4.4 Preparation of synthetic rHV1 peptides

Synthetic rHV1 peptides representing sequences 52–65, 40–65, 29–38, and 1–15 are synthesized by methods known in the art (Rink, Tetrahydron Letters 28, 3787, 1987).

4.5 Competitive ELISA

The antigenic determinants of rHV1 recognized by the anti-hirudin monoclonal antibodies are studied by a competitive ELISA test using microtiter plates coated with biotinylated rHV1 linked to avidin for MAb 4049-83-12 and with rHV1 for the three other MAbs. The percentage of inhibition obtained with rHV1 is compared to inhibition percentages measured with rHV1 analogues prepared by the procedures described above, such as synthetic rHV1 peptides, chemically modified rHV1, native rHV1 partially digested by staphylococcal V8 protease, and by recombinant hirudin variant PA (rHV3; Dodt et al., Biol. Chem. Hoppe-Seyler 367, 803, 1983).

The two-step competitive ELISA is done as follows: biotinylated rHV1 complexed with avidin (see example 4.1) or rHV1, respectively, in coating buffer is absorbed onto microtiter plates, and after overnight incubation at 40° C., the remaining free sites on the solid support are blocked by incubation with a 1% solution of BSA. The plates are then washed with PBS-Tween 0.1%. 50 μl of each purified anti-hirudin MAb (40 to 400 ng/ml) are incubated with 650 μl of a standard solution containing increasing amounts of either rHV1 or analogues (see above). After overnight incubation at 4° C., 200 μl of the mixture are added to each well and incubated for an additional hour. The wells are then washed five times, and 100 μl per well of goat anti-mouse antibody conjugated to alkaline phosphatase (dilution 1/1500) are added to the wells for 1.5 h. After washing, 150 μl per well of the substrate p-nitrophenylphospbate (1 mg/ml in diethanolamine buffer pH 9.8) are added to the wells. The change of colour, which is proportional to the amount of antibody reacting with the antigen bound to the solid phase, is monitored at 405 nm. All samples are run in triplicate.

Typical inhibition curves are obtained by plotting $B/Bo \times 100$ (percent bound) vs. the concentration of inhibitor present (Bo represents absorbance measured without rHV1 added to the antibody, and B, absorbance measured with various concentrations of rHV1 ). $IC_{50}$ represents the concentration of antigen which inhibits 50% of the binding of the antibody to the solid phase. $IC_{50}$ is calculated using an adaption of the curve fitting programm ENZFITTER (R. J. Leatberbarrow, Elsevier) based on a four parameter logistic curve: $U=(D-C)/1+(z/A)b)+C$, where U is the expected response for a dose z of the standard. The four parameters describe the shape of the curve, D and C give the upper and lower asymptote, and A is the dose of the mid-asymptote (Raab, Clin. Chem. 29, 1757, 1983). The IC$_{50}$ value, which represents the concentration of rHV1 which inhibits 50% of the binding of the antibody to the antigen bound to the microtiter plate, is calculated by the curve fitting program as described above.

The dissociation constants (K$_D$) of the MAbs are calculated according to the procedure of Friguet et al. (J. Immunol. Methods 77, 305, 1985).

The results are shown in FIG. 1 and in Table 5.

The absence of cross-reaction with the rHV1 peptide 29-38, which represents the "finger" domain, rules out this domain as a possible epitope although the linear peptide may differ extensively from the native conformation of this part of the molecule.

On the other hand, the three other MAbs recognize both C-terminal peptides 40–65 and 52–65 and show either a higher or comparable affinity for the S-carboxymethylated rHV1 compared to that of the native molecule.

TABLE 5

| | Competitive ELISA $IC_{50}$ (ng/ml) for | | | | |
|---|---|---|---|---|---|
| | Group I | Group II | | Group III | |
| Inhibitor | MAb 4049-83-12 | MAb 4114-96-1 | MAb 4120-37-7 | MAb 4102-21-14 | characterization of the hirudin analogues |
| rHV1 | 4 | 23 | 11 | 52 | |
| r-hirudin variant PA (rHV3) | >10'000 | >1'000 | >1'000 | >1'000 | residues different from rHV1: Ile 1, Thr 2, Lys 24, Gln 33, Lys 35, Asp 36, Gln 53, Pro 58, Asp 62, Ala 63, Asp 65, Glu 66 |
| rHV1 peptide 52-65 | >10'000 | 4 | 1 | 9 | |
| rHV1 peptide 40-65 | >10'000 | 11 | 3 | 20 | |
| rHV1 peptide 29-38 | >10'000 | ND | ND | >1'000 | |
| rHV1 peptide 1-15 | >10'000 | ND | ND | >1'000 | |
| S-CM-rHV1 | >1'000 | 6 | 13 | 22 | Reduced and S-carboxymethylated rHV1 |
| S-DABITC rHV1 | 56 | 3 | 1 | 5 | 97% of Val 1 and 90% of Lys 27 modified |
| S-DABITC rHV1 + TFA | 33 | ND | ND | 37 | Val 1 cleaved off; only Lys 27 modified |
| S-DAB-diazonium rHV1 | 9 | 53 | 5 | 65 | 20% of His 51, 45% of Tyr 63, 50% of Tyr 3 modified |
| biotinylated rHV1 | 4 | 18 | ND | 53 | 54% of Val 1, 37% of Lys 27, 39% of Lys 36 and 35% of Lys 47 modified |
| rHV1 + V8 protease (0.5 h) | 5 | >1'000 | 18 | 58 | 51% cleavage at Glu 43, 25% cleavage at Glu 61 |
| rHV1 + V8 protease (2 h) | 100 | >1'000 | 95 | 200 | 97% cleavage at Glu 43, 50% cleavage at Glu 61 |
| rHV1 + V8 protease (4 h) | 600 | ND | ND | ND | ND |
| rHV1 + endopeptidase (0.5 h) | 8 | ND | ND | ND | 100% cleavage at Lys 47; 78% cleavage at Lys 36 |
| rHV1 + endopeptidase (1.5 h) | 29 | 28 | 29 | 35 | 100% cleavage at Lys 47; 100% cleavage at Lys 36 |
| $K_D$(nM) | 0.6 | 3.2 | 1.5 | 7.1 | |

ND — not determined

With MAb 4049-83-12, the $IC_{50}$ value for rHV1 is 4 ng/ml. MAb 4049-83-12 detects rHV1 down to a level of around 1 ng/ml. The dissociation constant (KD) of the MAb is $6\times10^{-10}$M. The other three MAbs also cross-react with rHV1, although they have lower affinities ($K_D$ values from 1.5 to $7\times10^{-9}$M).

For MAb 4049-83-12, no cross-reactivity is observed between rHV1 and the four rHV1 synthetic peptides which cover most of the rHV1 sequence (residues 52–65, 40–65, 29–38 and 1–15). In addition, reduction and S-carboxymethylation of rHV1 , which destroys the three-dimensional structure of rHV1 by cleavage of the disulfide bonds, completely prevents the binding of the MAb. This suggests that MAb 4049-83-12 recognizes a discontinuous, conformation dependent epitope which is present only in the native rHV1 molecule and cannot be mimicked by peptides.

The treatment of rHV1 by DABITC, which modifies only the residues Val 1 and Lys 27, reduces the binding of MAb 4049-83-12 significantly. When S-DABITC rHV1 is treated by 90% TFA for 10 minutes at RT, the modified amino terminus at the position Val 1 is cleaved off, but the full binding of the MAb is not restored. This observation suggests that the N-terminus of rHV1 is not involved in the epitope recognized by MAb 4049-83-12, which is also confirmed by the absence of cross-reaction with the rHV1 peptide 1–15. On the other hand, the other three MAbs recognize rHV1 modified by S-DABITC better than unmodified rHV1.

The treatment of rHV1 by S-DAB-diazonium modifies mainly Tyr 3 and Tyr 63, whereas biotin-X-N-hydroxy-succinimide modifies mainly the N-terminus Val 1. Both treatments have almost no effect on the binding of MAb 4049-83-12, suggesting that residues at the N-terminal and C-terminal ends of rHV1 are not involved in the binding of MAb 4049-83-12.

Acetylation of rHV1, which converts the positively charged amino groups into neutral groups, has no effect on the binding of MAb 4049-83-12 whereas succinylation of rHV1, which introduces negative charges instead, reduces the binding of this MAb significantly. Since only the treatment with succinic anhydride and S-DABITC prevents the binding of MAb 4049-83-12 to rHV1, it seems likely that modification with these reagents triggers a conformational change of the molecule affecting the binding of this MAb, rather than the direct involvement of one of the amino residues of rHV1.

None of the four anti-hirudin MAbs recognizes rHV3 despite more than 80% homology between both hirudin variants (Dodt et al., Biol. Chem. Hoppe-Seyler 367, 803, 1983). The epitopes recognized by the MAbs seem to be rHV1 specific.

Finally, the digestion of native rHV1 by protease V8 cleaves mainly the C-terminal segment of rHV1 , i.e. cleavage after Glu 43 and Glu 61. With MAb 4049-83-12, the cross-reactivity of rHV1 treated for 0.5 h and 2 h decreases from 80% to 4%, while concomitantly 97% and 50% of the Glu 43-Gly 44 and Glu 62-Glu 63 bonds are cleaved. Moreover, when rHV1 is digested for 4.5 h with V8 protease, and the HPLC peaks corresponding to rHV1 fragments 1–43 and 44–61 are collected, dried and resuspended in buffer for ELISA analysis, no binding of MAb 4049-83-12 is observed. These results indicate that upon complete cleavage of the C-terminal domain, the well ordered structure of the epitope recognized by the MAb is destroyed. A strong influence of the V8 proteolysis on the binding properties of the other MAbs raised against rHV1 peptides is also observed, especially with MAb 4114-96-1.

Digestion of rHV1 by lysyl endopeptidase results in the complete cleavage of Lys 47-Pro 48 and Lys 36-Asn 37 after 90 min. After this time, the cross-reactivity drops to 14% for MAb 4049-83-12, whereas almost no effect is observed for the other MAbs.

4.6 Digestion of the rHV1/anti-hirudin monoclonal antibody complexes by V8 staphylococcal protease or by lysyl endopeptidase The formation of a complex between a monoclonal antibody and a protein-aceous antigen decreases the rate of proteolytic cleavage of the antigen, especially in the regions involved in the antigen-antibody contact (Jemmerson & Paterson, Science 232, 1001, 1986). Therefore, the effect of proteolysis is determined for the complexes formed between rHV1 and the anti-hirudin monoclonal antibodies.

To 23 μg (3.2 nmol) of rHV1, 315 pg (2.1 nmol) of each of the antihirudin monoclonal antibodies are added. After incubation at RT for 15 min, 7 μg of V8 protease or 2.5 μg of lysyl endopeptidase are added. The mixture (total volume 80 μl) is incubated for 30 min or 2 h at 37° C. The reaction is stopped by freezing the mixture at −20° C. Controls are: (i) digestion of rHV1 without an anti-hirudin MAb, (ii) digestion of rHV1 in the presence of an unspecific MAb, and (iii) digestion of the antihirudin MAbs in the absence of rHV1. The separation of the proteolytic fragments (2.7 μg) is done by reverse phase HPLC using the following gradient: Solvent A, 0.1% (v/v) anhydrous trifluoroacetic acid in water, solvent B, 0.1% (v/v) anhydrous trifluoroacetic acid in acetonitrile/water (6:4, v/v). Elution is carried out with a linear gradient with solvent B increasing from 20 to 80% in 30 min. The flow rate is 1 ml/min. The peptides are detected by measuring the absorbance at 220 nm. The identification of peptides is done by amino acid analysis and by amino-terminal analysis (see example 4.1).

When the rHV1/MAb 4049-83-12 complex is subjected to V8 proteolysis for 2 h, the HPLC peaks corresponding to the peptides 1–43, 44–61 and 44–65 completely disappear from the chromatogram whereas the peak corresponding to undigested rHV1, which is no more detectable in the controls, increases drastically. This clearly demonstrates that the cleavage after Glu 43 is prevented by the presence of this MAb, whereas cleavage after Glu 61 occurs to the same extent as in the controls. In this case, the cleavage is not complete so that undigested rHV1 appears on the chromatogram. Apparently, MAb 4049-83-12 recognizes an epitope of rHV1 in the N-terminal core domain comprising Glu 43 and Lys 47 (see below). On the other hand, when V8 proteolysis is carried out with rHV1 complexed with one of the other MAbs, the peaks corresponding to the peptides 62–65, 44–61 and 1–61 disappear from the chromatogram whereas the peak corresponding to peptide 44–65 increases significantly, indicating that cleavage occurs after Glu 43 but not after Glu 61. The absence of cleavage after Glu 61 is also observed when these MAbs are complexed with the rHV1 peptides 40–65 and 52–65, respectively, instead of rHV1. These data suggest that the binding domains of these MAbs are located close to the C-terminus of rHV1, very likely in the vicinity of residues 61–62.

These results are further confirmed by using lysyl endopeptidase to determine the extent of proteolysis of the rHV1-MAb complexes. rHV1 bound to MAb 4049-83-12 is fully protected from proteolysis during 6 h incubation with the enzyme. It elutes as one peak at the same retention time as untreated rHV1, whereas unprotected rHV1 elutes in two peaks corresponding to the peptides 48–65 and 1–47. Therefore it can be concluded that the cleavage after Lys 47 is completely prevented by the binding of the MAb. On the other hand, when MAb 4102-21-14 is bound to rHV1, proteolysis occurs as in the controls.

4.7. Double antibody sandwich ELISA

The epitope mapping is completed by experiments based on a double antibody sandwich ELISA described below to determine whether the anti-hirudin MAbs recognize overlapping epitopes.

Microtiter plates are coated with 0.5 μg/well of purified anti-hirudin MAb prepared in sodium carbonate buffer (50 mm, pH 9.6), and incubated overnight at 4° C. After the blocking and the washing steps (by BSA 1% and PBS-Tween 0.1%, respectively), increasing concentrations of rHV1 prepared in PBS-Tween 0.1% (0 to 100 ng/well) are added to the bound MAb and incubated for 1 h at RT. After washing, a biotinylated second anti-hirudin MAb is added to the plate (0.5 μg/well) and incubated for 2 h. Biotinylation of the MAbs is carried out essentially as described by Bayer et al. (Methods Enzymol. 62, 308, 1979). Biotin-X-N-hydroxy-succinimide ester (200 μg in 200 μl DMSO) is added to 5 mg of purified MAb in 5 ml PBS (pH 7.0) (13:1 mol/mol ratio). After 4 h at 4° C., the mixture is extensively dialyzed in PBS. Then, after washing, 100 μl of alkaline phosphatase conjugated streptavidin (diluted 1:2500) is added and incubated for 1.5 h at RT. After washing, the substrate is added and the absorbance is measured at 405 nm after different intervals of time, starting 15 min after the addition of the substrate.
The results are shown in Table 6.

TABLE 6

| MAb 1 (immobilized MAb) | Double antibody sandwich ELISA MAb 2 (free biotinylated MAb) [range in ng/ml] | | | | | | |
|---|---|---|---|---|---|---|---|
| | MAb 4049-83-12 | | MAb 4114-96-1 | | MAb 4120-37-7 | | MAb 4102-21-14 |
| MAb 4049-83-12 | − | 0 | + | 0.8–100 | + | 1.5–100 | + | 2.0–200 |
| MAb 4114-96-1 | + | 0.8–100 | − | 0 | − | 0 | − | 0 |
| MAb 4120-37-7 | + | 0.2–50 | − | 0 | − | 0 | − | 0 |
| MAb 4102-21-14 | + | 2.0–200 | − | 0 | − | 0 | − | 0 |

Symbols:
+ pairs of MAbs giving an absorbance at 405 nm superior to 3× the background
− pairs of MAbs giving an absorbance at 405 nm inferior to 3× the background
range: concentration of rHV1 measured by pairs of MAbs MAB 4049-83-12 combined with any of the other three MAbs is able to bind hirudin in a dose dependent manner with concentrations ranging from 0.2 to 200 ng/ml. These results demonstrate that the epitope recognized by MAb 4049-83-12 is distinct from the epitopes recognized by the other MAbs. On the other hand, MAb 4114-96-1, MAb 4120-37-7 and MAb 4102-21-14 are unable to bind rHV1 when used in combination, indicating clearly that they recognize overlapping epitopes. Furthermore, controls done by using pairs of identical MAbs (MAb1=MAb2) show no repetitive epitopes.

Example 5: Binding of the anti-hirudin monoclonal antibodies to the rHV1/α-thrombin complex The binding of the anti-hirudin MAbs to rHV1 complexed with α-thrombin is tested by a sandwich ELISA as described below.

Microtiter plates are coated with the anti-thrombin MAb EST 6 (0.6 μg/well; Bioscot, Edinburgh, UK). After overnight incubation at 4° C., blocking with BSA 1% and washing, the plates are incubated with α-thrombin (0.05 μg/well, 3000 NIH units/mg; CBR Laboratories) in PBS-BSA 0.1%, for the 2 h at RT. The plates are washed with PBS-Tween 0.1% and rHV1 is added at concentrations ranging from 0 to 1 μpg/well, and incubated for 1 h. After washing, biotinylated MAb 4049-83-12 is added (0.2 μg/well) and incubated for 1 h. Then, after washing, 100 μl of alkaline-phosphatase conjugated streptavidin (dilution 1/2500, Calbiochem) are added for 1.5 h, followed by washing with the substrate. In addition to the negative controls, a positive control is made by adding biotinylated rHV1 instead of unmodified rHV1 , which is detected with the avidin conjugate and thus confirms the binding of rHV1 to αthrombin (in this control no MAb is added).

None of the four anti-hirudin MAbs is capable of binding to rHV1 complexed to α-thrombin. Biotinylated rHV1 revealed by alkaline-phosphatase conjugated avidin is used as positive control to confirm that rHV1 is indeed complexed with α-thrombin.

Example 6: Quantitative determination of rHV1 in a sandwich enzyme-linked immunosorbent assay (ELISA)

rHV1 can be determined in buffer or biological fluids, e.g. urine, plasma etc., in a quantitative double antibody sandwich ELISA using the specific monoclonal antibody MAb 4049-83-12 as capture antibody and affinity purified anti-hirudin sheep serum (Spinner et al., J. Immunol. Methods 87, 79, 1986) as second labelled antibody. Only free rHV1 in its native confirmation is determined by the assay, whereas rHV1 once bound to α-thrombin is not measured.

A microtiter plate is coated with 100 μl per well of a solution of MAb 4049-83-12 (10 μg/ml) in coating buffer, incubated overnight at 4° C. in a moist chamber and washed five times with PBS-Tween 0.1%. The wells are allowed to dry, filled with 200 μl per well of PBS-BSA 1%, incubated 1–2 h at RT, and washed five times with PBS-Tween 0.1%. 100 μl per well of standard solutions of rHV1 (i.e. 0; 0.19; 0.39; 0.78; 1.56; 3.12; 6.25; 12.5; 25.0; 100.0 ng/ml in PBS-Tween 0.1%) are added and samples diluted accordingly in PBS-Tween 0.1 They are incubated 2 h at RT and washed five times with PBS-Tween 0.1 Then, 100 μl per well of biotinylated sheep anti-hirudin polyclonal antibodies (5 μg/ml) in PBS-Tween 0.1% are added. After 2 h incubation at RT, the samples are washed five times with PBS-Tween 0.1% and 100 μl per well of avidinalkaline phosphatase conjugate (dilution 1/2500 in PBS-Tween 0.1%) are added. The samples are incubated 90 min at RT and washed with PBS-Tween 0.1%. The plate is developed by incubating the enzyme with 150 μl of substrate solution (p-nitrophenyl phosphate 1 mg/ml in diethanolamine buffer) for 15 to 30 min at RT in the dark. The reaction is stopped by adding 50 μl of NaOH 3M and the optical density is read at 405 nm.

The linear range of detection is between 0.2–50 ng/ml of rHV1.

Example 7: Test kit for an ELISA for rHV1

A test kit for the ELISA described in example 6 contains:

polyvinyl chloride microtiter plates
20 ml of monoclonal antibody MAb 4049-83-12 (10 μg/ml) in coating buffer
20 ml of anti-hirudin polyclonal antibodies in PBS-Tween 0.1% (5 μg/ml)
2 ml standard solution containing 5 μg rHV1
300 ml of PBS-Tween 0.1%
300 ml of PBS-BSA 1%
50 ml of p-nitrophenyl phosphate (1 mg/ml) in diethanolamine buffer (10%, 0.5 mM $MgCl_2$, 0.02% $NaN_3$, adjusted to pH 8.9 with HCl)
calibration curve
colour intensity scale
instruction manual.

Example 8: Antidote activity of the anti-hirudin monoclonal antibodies

The anti-hirudin MAbs are tested in vitro for their ability to neutralize the anticoagulation activity of hirudin towards alpha-thrombin using the clotting assay described by Fenton & Fasco (Thrombosis Res. 4, 809, 1974). Briefly, 50 μl of purified MAb at increasing concentrations are incubated for 10 min with various concentrations of rHV1 (0–85 nM, 0–600 ng/ml). Then, 50 μl of a freshly prepared α-thrombin solution (2.4 μg/ml, 67 nM, in 0.01M imidazole buffer pH 7.4 supplemented with 0.15M NaCl, 0.01M $CaCl_2$ and 0.6% (w/v) polyethylene glycol 6000) are added, and after 1 min at 37° C., 350 μl of prewarmed fibrinogen grade L (3.2 mg/ml, Kabi Vitrum) are added. The clotting time is measured in an Amelung coagulometer KC 1A at 37° C. A control is run in the absence of rHV1. In some experiments, rHV1 is incubated with α-thrombin for 1 min prior to the addition of increasing concentrations of the MAb.

Figure 2:
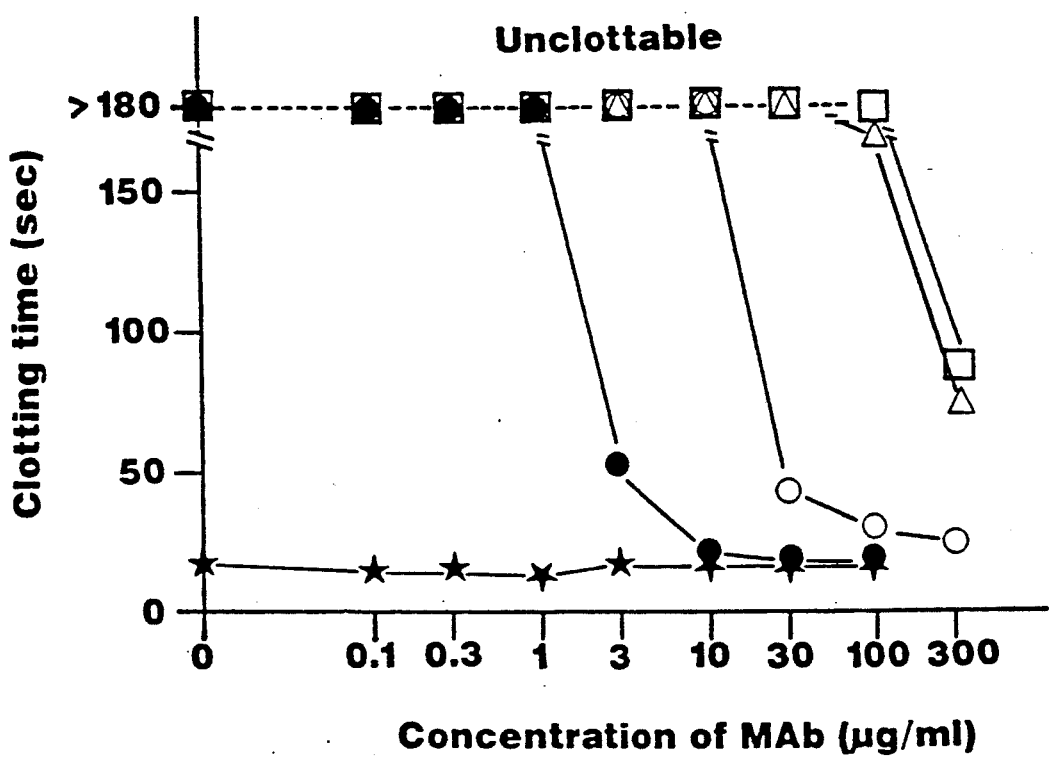
FIG. 2: Neutralization capacity of the anti-hirudin monoclonal antibodies (see example 8)

The results are shown in FIG. 2. MAb 4049-83-12 can completely neutralize rHV1. Even at a hirudin concentration of 85 nM (corresponding to a slight excess of hirudin over thrombin) where clotting time is infinite, the anticoagulant activity of hirudin is totally neutralized by equimolar concentration of MAb 4049-83-12 binding sites (around 5–10 μg/ml). Furthermore, the addition of a large excess of MAb 4049-83-12 (100 μg/ml) to rHV1 already complexed to α-thrombin can restore partially the thrombin enzymatic activity. MAb 4120-37-7 is also capable of neutralizing the activity of rHV1, although the antibody concentration needed to completely neutralize rHV1 is ten times higher than that of MAb 4049-83-12.

We claim:

1. A hybridoma cell line which is prepared by a process for the preparation of hybridoma cells which secrete monoclonal antibodies specific for an epitope of recombinant hirudin variant HV1 (rHV1) comprising at least the amino acid residues 43 and 47, comprising the steps of:
   immunizing a mammal with an immunogenic hirudin variant HV1 (rHV1)-conjugate,
   fusing the antibody-producing cells of said mammal with cells of a continuous cell line,
   cloning the hybridoma cells obtained in the fusion, and
   selecting the cell clones secreting the monoclonal antibodies specific for an epitope of recombinant hirudin variant HV1 (rHV1) comprising at least the amino acid residues 43 and 47.

2. A hybridoma cell with the designation 4049-83-12 (ECACC 8808 2504).

3. A monoclonal antibody which recognizes an epitope of recombinant hirudin variant HV1 (rHV1) comprising the amino acid residues 43 and 47.

4. A derivative of a monoclonal antibody according to claim 3, which retains its specificity for the antigenic determinants of said hirudin.

5. A derivative of a monoclonal antibody according to claim 4, which is a conjugate with an enzyme, a fluorescence marker, a chemiluminescent marker, a metal chelate, avidin, or biotin.

6. A derivative of a monoclonal antibody according to claim 4, which is radioactively labelled.

7. A derivative of a monoclonal antibody according to claim 4, which is a fragment.

8. A derivative according to claim 4 of the monoclonal antibody with the designation MAb 4049-83-12.

9. A method for the qualitative and quantitative determination of hirudin comprising the steps of:
   (a) incubating a test sample with a monoclonal antibody according to claim 3, and
   (b) determining the presence or absence of the immune complex of hirudin with the monoclonal antibody formed and, optionally, the amount of the immune complex of hirudin with the monoclonal antibody formed.

10. A method for the qualitative and quantitative determination of hirudin comprising the steps of:
    (a) incubating a test sample with a derivative of a monoclonal antibody according to claim 4, and
    (b) determining the presence or absence and/or the amount of the immune complex of hirudin with the derivative formed.

11. A test kit for the qualitative and quantitative determination of hirudin comprising a monoclonal antibody according to claim 3, and, optionally, other monoclonal or polyclonal antibodies, adjuncts, or mixtures there of.

12. A test kit for the qualitative and quantitative determination of hirudin comprising a derivative of a monoclonal antibody and according to claim 4, and, optionally, other monoclonal or polyclonal antibodies, adjuncts, or mixture there of.

13. A monoclonal antibody with the designation MAb 4049-83-12.

* * * * *